(12) United States Patent
O'Lenick

(10) Patent No.: US 8,674,049 B1
(45) Date of Patent: Mar. 18, 2014

(54) SILICONE CONTAINING AROMATIC FILM FORMING POLYMERS

(75) Inventor: Thomas G. O'Lenick, Dacula, GA (US)

(73) Assignee: Surfatech Corporation, Lawrenceville, GA (US)

( * ) Notice: Subject to any disclaimer, the term of this patent is extended or adjusted under 35 U.S.C. 154(b) by 102 days.

(21) Appl. No.: 13/507,580

(22) Filed: Jul. 12, 2012

(51) Int. Cl.
*C08G 77/04* (2006.01)

(52) U.S. Cl.
USPC .......................................................... 528/10

(58) Field of Classification Search
None
See application file for complete search history.

(56) References Cited

U.S. PATENT DOCUMENTS

| | | | | |
|---|---|---|---|---|
| 4,301,046 A | * | 11/1981 | Schlossman | 523/105 |
| 5,210,133 A | * | 5/1993 | O'Lenick, Jr. | 525/54.1 |
| 5,538,717 A | * | 7/1996 | La Poterie | 424/61 |
| 7,524,919 B2 | * | 4/2009 | Hoover et al. | 528/196 |

* cited by examiner

*Primary Examiner* — Robert S Loewe

(57) ABSTRACT

The present invention is directed to polymers that are useful in nail polish applications. The specific film forming polyester polymers that are liquids in solvents like butyl acetate, form a uniform film upon application when in a solvent (most commonly butyl acetate), evaporates under atmospheric conditions and at the same time can be removed easily and thoroughly by application of a solvent like acetone. The polymers of the present invention having a silicone portion contained therein provide improved flexibility, tear resistance and superior aesthetics.

17 Claims, No Drawings

SILICONE CONTAINING AROMATIC FILM FORMING POLYMERS

RELATED APPLICATIONS

None

GOVERNMENT SPONSORSHIP

None

FIELD OF THE INVENTION

The present invention is directed to polymers that are useful in nail polish applications. The specific film forming polyester polymers that are liquids in solvents like butyl acetate, form a uniform film upon application when in a solvent (most commonly butyl acetate), evaporates under atmospheric conditions and at the same time can be removed easily and thoroughly by application of a solvent like acetone. The polymers have as critical part of the polymer a silicone portion which provides flexibility, tear resistance and superior aesthetics.

BACKGROUND OF THE INVENTION

The cosmetic placing of color onto the nail of humans has loon been a desirable and part of the cosmetic world. The physical and chemical demands of color so applied are dramatic. Specifically, the following considerations need to be addressed (1) how to apply color in a film that is easy to applied in a process at ambient conditions; (2) how to obtain a cosmetically acceptable film, in terms of color clarity, and gloss; (3) how to maintain the film and the desirable properties that the consumer demands over a period of time that the film remains on the skin; (4) how to assure resistance to environmental insults the nails are subjected to during the lifetime of the polish; (5) and how to thoroughly remove the film efficiently and thoroughly when the consumer desires the removal, and finally how to do this in a cost effective way.

It must be clearly understood that the process of decorative application of color to the nails by a consumer is fundamentally different from painting a wall or other permanent film applications. Unlike the application of paint, nail colors need to be removable thoroughly and effectively at the whim of the consumer. The color is in many regards a fashion item and can change quite often in a short period of time.

This ability to be easily removed at any time, coupled with the need to be accomplished by the consumer in a home environment, places limitations upon the type of process that can be used, in terms of application technique (limited to brush application) at ambient conditions and using no special equipment.

In addition to need for facile application and removal as desired by the consumer, the films and the colors and other ingredients present in the film need to apply in a uniform film and remain functional and cosmetically acceptable on the nail in terms of scuffing, breaking when struck, pliable over the period of time during which they are on the nails. The film that forms in the above process must possess specific cosmetic benefits, including ability to disperse colors, be scuff resistant, resistant to cracking when struck, remain pliable and cosmetically appealing. One of the major properties the consumers finds appealing is gloss. Gloss in a film of this type is generally difficult to attain by adding ingredients. The inclusion of an aromatic components directly into the film. This is generally accomplished by adding into the reaction mixture, trimellitic anhydride. This aromatic anhydride alters the refractive index of the film providing gloss.

U.S. Pat. No. 4,301,046 issued in November 1981 to Mitchell Schlossman, a pioneer in the field, entitled Universal nail polish using polyester resin disclosed a nail polish is made from 92% to 96% ingredients including a film former, colorant, plasticizer and solvent; and 4% to 8% polyester resin made from 2,2,4-trimethyl-1,3-pentanediol, isophthalic acid-85, and trimellitic anhydride, having an acid value of 75-85 and a viscosity of 125-175 centipoise. In another example, the polyester is made from 50.932% 2,2,4 trimethyl-1,3-pentanediol, 27.579% isophthalic acid-85, 0.186% dibutyl tin oxide catalyst and 21.303 trimellitic anhydride, having an acid value of 80 and a viscosity of 150 centipoise.

The inclusion of silicone as a reactant in the polymer mixture results in many highly desirable attributes and makes a more cosmetically appealing film. Firstly, polymers containing silicone result in better more uniform films when applied to the nail. Not wanting to be bound by a single theory, this appears to be the result of a lowering of the surface tension of the film when applied. Secondly, polymers containing silicone are more flexible when applied to the nails, this makes them less likely to break upon a physical insult, and less likely to undergo a cut damage when sharp items are encountered by the film. Finally, polymers containing silicone are more easily removed with acetone, in part because they are easily wet out by the solvent in silicone is present, a result related to the low surface tension of silicone containing films, compared to non silicone containing films of comparable composition.

THE INVENTION

Objective of the Invention

The present invention is drawn to a polymer that contains silicone within the polymer backbone. This results in new heretofore unattainable properties in nail polish.

In addition, the present invention is directed to a process for treating nails, which comprises contacting the nails with the polymers of the present invention additionally containing colors. Other Objectives of the invention will become clear as one reads the specification of the invention.

All patents referenced herein are incorporated herein by reference to the extent allowed. Unless specifically stated elsewhere all temperatures are in degrees C., and all % given are % by weight.

SUMMARY OF THE INVENTION

The present invention is directed to a film-forming polymer which is synthesized by the esterification reaction of (1) a difunctional organic polyol; (2) a difunctional silicone polyol a difunctional; (3) an organic acid (4) a difunctional silicone and (5) trimellitic anhydride. By film forming is meant a polymer that is liquid at ambient temperatures, at 70-80% by weight polymer in 20-30% volatile solvent, typically acetone or butyl acetate but forms a uniform film when the solvent evaporates. The liquid solution at obtained by addition of solvent ambient temperature, is transformed when the solvent evaporates into a uniform film that adheres to the nail, and is removable using acetone in a subsequent step.

DETAILED DESCRIPTION OF THE INVENTION

The present invention is directed to a film-forming polymer which is synthesized by the esterification reaction of (a) a difunctional organic polyol selected from the group consisting of

 and 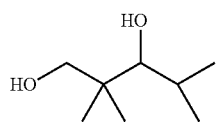

and mixtures thereof;

(b) a difunctional silicone polyol which conforms the following structure;

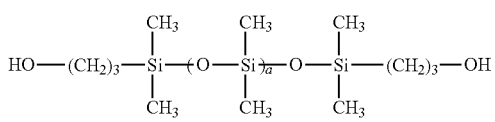

wherein;
a is an integer ranging from 1 to 20;

(c) a difunctional organic acid selected from the group consisting of;

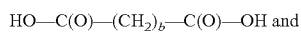

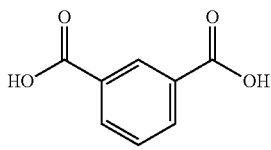

mixtures thereof;
wherein;
b is an integer ranging from 1 to 10;

(d) a difunctional silicone ester which conforms the following structure;

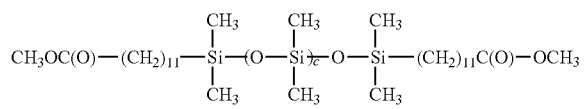

wherein;
c is an integer ranging from 1 to 20;
and
(e) trimellitic anhydride conforming the following structure;

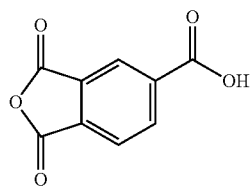

The present invention is also directed to a process for applying color to the nail or skin which comprises of a film-forming polymer which is made by the reaction of;

(a) a difunctional organic polyol selected from the group consisting of

 and 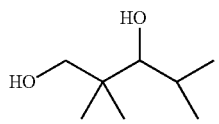

(b) a difunctional silicone polyol which conforms the following structure;

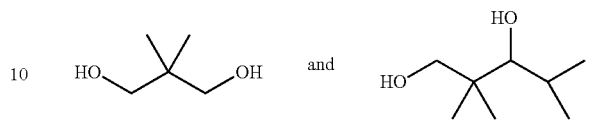

wherein;
a is an integer ranging from 1 to 20;
(c) a difunctional organic acid selected from the group consisting of;

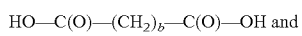

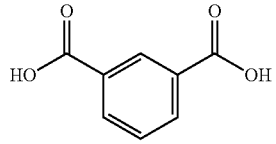 [SMILES: O=C(O)c1cccc(C(=O)O)c1]

wherein;
b is an integer ranging from 1 to 10;
(d) a difunctional silicone acid which conforms the following structure;

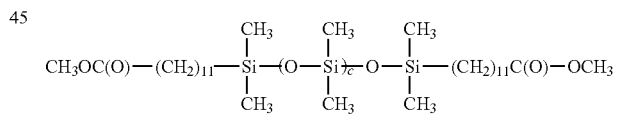

wherein;
c is an integer ranging from 1 to 20;
and
(e) trimellitic anhydride conforming the following structure;

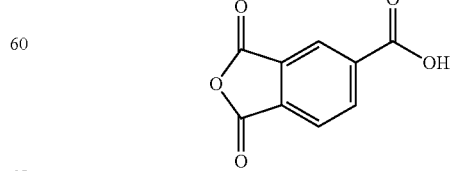

additionally containing color and solvent.

The proper selection raw materials used to make the polymers of the present inventions determine the properties of the film that result. The polymers of the present invention make films, which are of interest in making nail polish.

In order to make polymers suitable for the application, the polymer must be a liquid when present in butyl acetate, dry to a film upon evaporation, then become soluble again in solvents like acetone. It is this solubility which allows for application and removal, but as importantly, the polymer needs to have attributes the consumer finds desirable like gloss, resistance to scuff and flexibility. The applicant has surprisingly found that incorporating silicone containing reactants in the polymers of the present invention provides great scuff residence, great spread ability when compared to the polymer with the silicone absent, wear properties when applied to the nail and the ability to flow on the nail are all improved.

The inclusion of the trimellitic anhydride in the polymer increases the refractive index of the compounds of the present invention providing much desired gloss. Furthermore, the rigidity of the trimellitic repeat unit improves the durability of the film. It is well known when rigid units, in a polymer backbone, increase the glass transition temperature ($T_g$).

The compounds of the present invention are polyesters and as such avoid the undesirable properties of being made from vinyl reactive monomers, which need to be removed to vanishingly low concentrations to avoid potentially toxic products present in the polymers of the present invention.

PREFERRED EMBODIMENTS

In a preferred embodiment the film-forming polymer which is made by the reaction of;

(a) between 10 and 63% by weight of a difunctional organic polyol selected from the group consisting of;

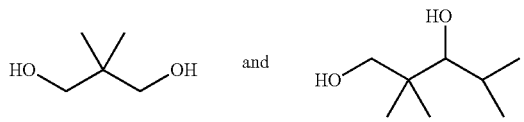

(b) a difunctional organic acid selected from the group consisting of;

HO—C(O)—(CH$_2$)$_b$—C(O)—OH and

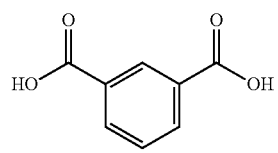

wherein;

b is an integer ranging from 1 to 10;

(c) between 2 and 10% by weight of a difunctional silicone polyol which conforms the following structure;

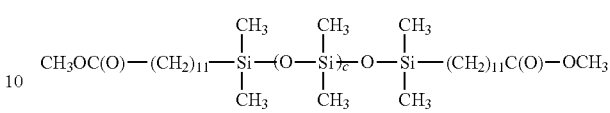

wherein c is an integer ranging from 1 to 20; and (d) 30-60% by weight of trimellitic anhydride conforming the following structure;

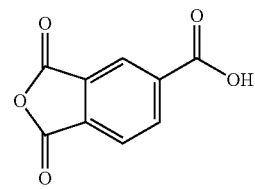 [SMILES: O=C(O)c1ccc2c(c1)C(=O)OC2=O]

In a preferred embodiment process the film-forming polymer additionally contains a solvent selected from the group consisting of butyl acetate and acetone.

In a preferred embodiment a is 1.
In a preferred embodiment a is 1.
In a preferred embodiment a is 5.
In a preferred embodiment a is 10.
In a preferred embodiment a is 20.
In a preferred embodiment b is 4.
In a preferred embodiment c is 1.
In a preferred embodiment c is 1.
In a preferred embodiment c is 5.
In a preferred embodiment c is 10.

EXAMPLES

Difunctional Organic Polyol

Example 1

Neopentyl Glycol

Neopentyl glycol is an item of commerce available from a variety of sources including BASF. It conforms to the following structure:

It has a CAS number of 126-30-7.

Example 2

2,2,4-trimethyl-1,3-pentanediol 2 2,2,4-trimethyl-1,3-pentanediol is an item of commerce available from a variety of sources including Sigma Aldrich. It conforms to the following structure:

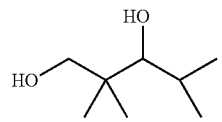

The CAS number is 144-19-4.

Difunctional Silicone Polyol

Examples 3-6

Difunctional silicone polymers are items of commerce commercially available from Siltech LLC of Lawrenceville Ga. They conform to the following structure;

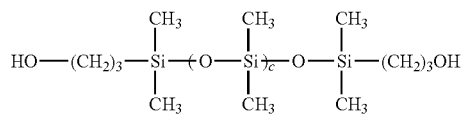

wherein
c is an integer ranging from 1 to 20;
a is an integer ranging from 1 to 20;

| Example | A value |
|---------|---------|
| 3 | 1 |
| 4 | 5 |
| 5 | 10 |
| 6 | 20 |

Difunctional Organic Acids

Examples 7-11

Difunctional organic acids are items of commerce commercially available from BASF. They conform to the following structure;

$$HO—C(O)—(CH_2)_b—C(O)—OH$$

wherein;
b is an integer ranging from 1 to 10.

| Example | B | Molecular Weight (g/mol) |
|---------|-----|--------------------------|
| 7 | 5 | 237 |
| 8 | 8 | 367 |
| 9 | 15 | 676 |
| 10 | 23 | 1027 |
| 11 | 25 | 1116 |

Example 12

Isophthalic Acid

Isophthalic acid is an item of commerce commercially available from a number of suppliers including Tianjin Ruihui chemicals import & export co., ltd.

It conforms to the following structure:

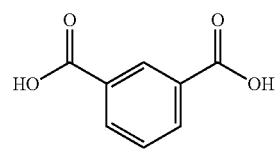 [SMILES: O=C(O)c1cccc(C(=O)O)c1]

It has a CAS number of 121-91-5.

Difunctional Silicone Acid

Examples 13-16

Difunctional silicone polymers are items of commerce commercially available from Siltech LLC of Lawrenceville Ga. They conform to the following structure;

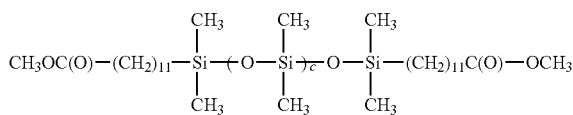

wherein;
c is an integer ranging from 1 to 20;

| Example | c value |
|---------|---------|
| 13 | 1 |
| 14 | 5 |
| 15 | 10 |
| 16 | 20 |

Example 17

Trimellitic Anhydride

Trimellitic anhydride is an item of commerce commercially available from Sigma Aldrich. It conforms the following structure;

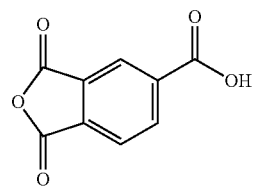 [SMILES: O=C(O)c1ccc2c(c1)C(=O)OC2=O]

CAS no. 552-30-7
EINECS 209-008-0

Example 18

Butyl Acetate

Butyl acetate is an item of commerce commercially available from a variety of sources including Sciencelab.com, Inc. It conforms to the following structure;

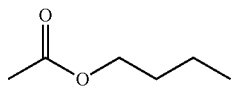

It has a CAS number of 123-86-4.

Example 19

Acetone

Acetone is an item of commerce commercially available from a variety of sources including Sigma Aldrich.

It has a CAS number of 67-64-1.

By color is meant colors allowed by the Food and Drug Administration (FDA)

Color Additives Permitted for Use in Cosmetics: Table Apr. 30, 2008; Updated Jun. 20, 2008 and Feb. 22, 2010

The tables below are provided as a supplement to the information in the Summary of Color Additives Listed for Use in the United States in Food, Drugs, Cosmetics, and Medical Devices. They are intended for quick reference to help in determining which color additives may be used in different types of cosmetics, as provided for in Title 21 of the Code of Federal Regulations (CFR), Subpart C of Part 73 (Listing of Color Additives Exempt from Certification), Subpart C of Part 74 (Listing of Color Additives Subject to Certification), and Subparts C and D of Part 82 (Listing of Certified Provisionally Listed Colors and Specifications). For additional information on the permitted use, specifications, and restrictions that apply to each color additive, please refer to the appropriate listing regulation, using the links provided in the tables. For more information on the use of color additives in cosmetics in general, please see Color Additives and Cosmetics.

Color Additives that are Exempt from Certification and Permitted for Use in Cosmetics

| (21 CFR Part 73 Subpart C - Cosmetics) | | | | |
|---|---|---|---|---|
| Color Additive | Eye Area | Generally (Includes Lipsticks) | External Use | 21 CFR Section |
| Aluminum powder | Yes | No | Yes | 73.2645 |
| Annatto | Yes | Yes | Yes | 73.2030 |
| Bismuth citrate | No | No | Subject to limitations | 73.2110 |
| Bismuth oxychloride | Yes | Yes | Yes | 73.2162 |
| Bronze powder | Yes | Yes | Yes | 73.2646 |
| Caramel | Yes | Yes | Yes | 73.2085 |
| Carmine | Yes | Yes | Yes | 73.2087 |
| β-Carotene | Yes | Yes | Yes | 73.2095 |
| Chromium hydroxide green | Yes | No | Yes | 73.2326 |
| Chromium oxide greens | Yes | No | Yes | 73.2327 |
| Copper powder | Yes | Yes | Yes | 73.2647 |
| Dihydroxyacetone | No | No | Subject to limitations | 73.2150 |
| Disodium EDTA-copper | No | No | Subject to limitations | 73.2120 |
| Ferric ammonium ferrocyanide | Yes | No | Yes | 73.2298 |
| Ferric ferrocyanide | Yes | No | Yes | 73.2299 |
| Guaiazulene | No | No | Yes | 73.2180 |
| Guanine | Yes | Yes | Yes | 73.2329 |
| Henna | No | No | Subject to limitations | 73.2190 |
| Iron oxides | Yes | Yes | Yes | 73.2250 |
| Lead acetate | No | No | Subject to limitations | 73.2775 |
| Luminescent zinc sulfide | No | No | Subject to limitations | 73.2995 |
| Manganese violet | Yes | Yes | Yes | 73.2775 |
| Mica | Yes | Yes | Yes | 73.2496 |
| Potassium sodium copper chlorophyllin (chlorophyllin-copper complex) | No | No | Subject to limitations | 73.2125 |
| Pyrophyllite | No | No | Yes | 73.2400 |
| Silver | No | No | Subject to limitations | 73.2500 |
| Titanium dioxide | Yes | Yes | Yes | 73.2575 |
| Ultramarines | Yes | No | Yes | 73.2725 |
| Zinc oxide | Yes | Yes | Yes | 73.2991 |

| Additives That Are Subject to Certification and Permitted for Use in Cosmetics* Includes Straight Colors and Lakes (21 CFR Part 74 Subpart - Cosmetics, and 21 CFR Part 82 Subpart C - Drugs and Cosmetics and Subpart D - Externally Applied Drugs and Cosmetics) | | | | |
|---|---|---|---|---|
| Color Additive | Eye Area** | Generally (Includes Lipsticks) | External Use | 21 CFR Section |
| D&C Black No. 2 | Subject to Limitations | Subject to Limitations | Subject to Limitations | 74.2052 |
| D&C Black No. 3 | Subject to Limitations | No | Subject to Limitations | 74.2053 |
| FD&C Blue No. 1 | Yes, also Al lake | Yes | Yes | 74.2101 |
| D&C Blue No. 4 | No | No | Yes | 74.2104 |
| D&C Brown No. 1 | No | No | Yes | 74.2151 |
| FD&C Green No. 3 | No | Yes | Yes | 74.2203 |
| D&C Green No. 5 | Yes | Yes | Yes | 74.2205 |
| D&C Green No. 6 | No | No | Yes | 74.2206 |
| D&C Green No. 8 | No | No | Subject to Limitations | 74.2208 |
| D&C Orange No. 4 | No | No | Yes | 74.2254 |
| D&C Orange No. 5 | No | Subject to Limitations | Yes | 74.2255 |

| Color Additive | Eye Area** | Generally (Includes Lipsticks) | External Use | 21 CFR Section |
|---|---|---|---|---|
| D&C Orange No. 10 | No | No | Yes | 74.2260 |
| D&C Orange No. 11 | No | No | Yes | 74.2261 |
| FD&C Red No. 4 | No | No | Yes | 74.2304 |
| D&C Red No. 6 | No | Yes | Yes | 74.2306 |
| D&C Red No. 7 | No | Yes | Yes | 74.2307 |
| D&C Red No. 17 | No | No | Yes | 74.2317 |
| D&C Red No. 21 | No | Yes | Yes | 74.2321 |
| D&C Red No. 22 | No | Yes | Yes | 74.2322 |
| D&C Red No. 27 | No | Yes | Yes | 74.2327 |
| D&C Red No. 28 | No | Yes | Yes | 74.2328 |
| D&C Red No. 30 | No | Yes | Yes | 74.2330 |
| D&C Red No. 31 | No | No | Yes | 74.2331 |
| D&C Red No. 33 | No | Subject to Limitations | Yes | 74.2333 |
| D&C Red No. 34 | No | No | Yes | 74.2334 |
| D&C Red No. 36 | No | Subject to Limitations | Yes | 74.2336 |
| FD&C Red No. 40 | Yes, | Yes | Yes | 74.2340 |
| D&C Violet No. 2 | No | No | Yes | 74.2602 |
| Ext. D&C Violet No. 2 | No | No | Yes | 74.2602a |
| FD&C Yellow No. 5 | Yes, also Al lake | Yes | Yes | 74.2705 |
| FD&C Yellow No. 6 | No | Yes | Yes | 74.2706 |
| D&C Yellow No. 7 | No | No | Yes | 74.2707 |
| Ext. D&C Yellow No. 7 | No | No | Yes | 74.2707a |
| D&C Yellow No. 8 | No | No | Yes | 74.2708 |
| D&C Yellow No. 10 | No | Yes | Yes | 74.2710 |
| D&C Yellow No. 11 | No | No | Yes | 74.2711 |

*Includes straight colors and lakes
**Excludes lakes except where noted. Only aluminum lakes on alumina are permitted for designated lakes.

Preparation of the Polymers of the Present Invention

The compounds of the present invention are prepared by an esterification reaction.

General Procedure

To a suitable reaction flask, able to heat contents to 200° C. with good agitation and the ability to distill off water is added the specified number of grams of the specified difunctional glycol Examples 1-2); next add the specified number of grams of the specified difunctional silicone glycol Examples (3-6); next add the specified number of grams of the specified organic acid Examples (7-12); next add the specified number of grams of the specified trimellitic anhydride (Examples 17); finally add 0.2 grams of stannous oxylate. Heat to 170-190° C. and react for 4-6 hours, monitoring acid value. When acid value approaches 80 mg KOH/gm, cool the reaction mass. Once cool add 300 grams of butyl acetate.

| Examples | Difunctional Glycol | | Difunctional Silicone Glycol | | Organic Acid | | Difunctional Silicone | | Trimetillic Anhydride | |
|---|---|---|---|---|---|---|---|---|---|---|
|  | Ex | g | Ex | g | Ex | g | Ex | g | Ex | G |
| 20 | 1 | 294 | 3 | 229 | 7 | 42 | 13 | 29 | 17 | 407 |
| 21 | 2 | 419 | 4 | 94 | 12 | 25 | 14 | 95 | 17 | 367 |
| 22 | 1 | 275 | 5 | 138 | 9 | 120 | 15 | 129 | 17 | 405 |
| 23 | 1 | 333 | 3 | 54 | 11 | 184 | 13 | 27 | 17 | 402 |
| 24 | 2 | 419 | 4 | 94 | 12 | 25 | 14 | 95 | 17 | 367 |
| 25 | 1 | 305 | 5 | 150 | 7 | 36 | 15 | 141 | 17 | 368 |
| 26 | 2 | 369 | 6 | 230 | 11 | 30 | 16 | 35 | 17 | 337 |
| 27 | 1 | 382 | 3 | 63 | 12 | 32 | 13 | 32 | 17 | 491 |
| 28 | 2 | 379 | 4 | 85 | 9 | 118 | 14 | 118 | 17 | 332 |
| 29 | 1 | 295 | 5 | 148 | 8 | 55 | 15 | 139 | 17 | 363 |
| 30 | 2 | 438 | 3 | 51 | 12 | 26 | 14 | 100 | 17 | 415 |
| 31 | 1 | 389 | 3 | 63 | 7 | 24 | 13 | 24 | 17 | 415 |
| 32 | 2 | 473 | 3 | 55 | 7 | 28 | 13 | 28 | 17 | 415 |
| 33 | 1 | 211 | 3 | 25 | 7 | 12 | 13 | 12 | 17 | 415 |
| 34 | 2 | 252 | 4 | 30 | 12 | 16 | 15 | 16 | 17 | 415 |

The products as prepared have 25% butyl acetate added to make a liquid solution at ambient temperature. When the solvent evaporates, a uniform film is left which adheres to the nail, and is removable using acetone.

APPLICATIONS EXAMPLES

The polymers of the present invention can be tailored for particular functionality as requested by the consumer. Firstly, as the concentration of aromatic compound (trimellitic anhydride and isophthalic acid), the refractive index of the film increases and the gloss increases. Matte films result when the concentration falls below 20% by weight. Secondly, as the concentration of the silicone difunctional silicone glycol increases in the polymer, the plasticity of the dry down film increases. Thirdly, if the concentration of the silicone polymer containing carboxyl groups is increases, the dry time of the film increases. This is because a C11 fatty group in incorporated into the molecule. Fourthly, it the organic acid concentration is increased, the film becomes more brittle. Brittle nail polishes crack and are not acceptable to the consumer.

It must be clearly understood that the films provided by the polymers of the present invention are by nature transient films that is the materials are low viscosity liquids when the butyl acetate is present. They spread easily on the nail. Incorporating silicone into the polymer enhances this spreadbility, as the resulting surface tension of the polymer in butyl acetate decreases from 32 dynes/cm to 25 dynes/cm. Once the film forms, it needs to efficiently disperse the color and once again silicone in the molecule helps in this regard. When the nail polish has outlived the consumer's interest in it, the film must be effectively removed with solvents like acetone. If the film is too heavily crosslinked, the film deposited will be very difficult to remove.

In short, the perfect nail polish is a balancing act. Balancing the ease of application, spreadability, color deposition, gloss, flexibility and ease of removal. Silicone in the molecule results in an ability to enhance the various properties demanded by the consumer, and adds an overall unexpected improvement in many of the properties when made in accordance with the teachings of the present invention.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

The invention claimed is:

1. A silicone containing film-forming polymer which is made by the esterification reaction of;
  (a) a difunctional organic polyol selected from the group consisting of

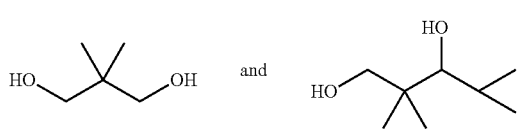

and mixtures thereof;

(b) a difunctional silicone polyol which conforms the following structure;

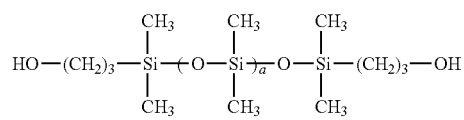

wherein;
  a is an integer ranging from 1 to 20;
  (c) a difunctional organic acid selected from the group consisting of;

HO—C(O)—(CH$_2$)$_b$—C(O)—OH and

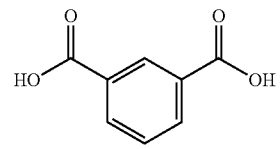 [SMILES: O=C(O)c1cccc(C(=O)O)c1]

and mixtures thereof;
  wherein;
  b is an integer ranging from 1 to 10;
  (d) a difunctional silicone acid which conforms the following structure;

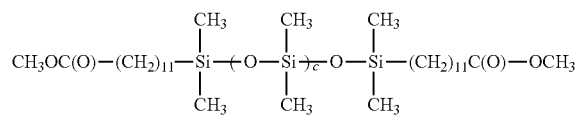

wherein;
  c is an integer ranging from 1 to 20;
  and
  (e) trimellitic anhydride conforming the following structure;

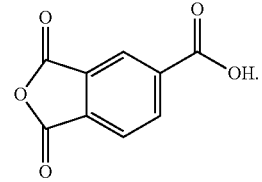 [SMILES: O=C(O)c1ccc2c(c1)C(=O)OC2=O]

2. A silicone film forming polymer of claim 1 wherein a is 1.

3. A silicone film forming polymer of claim 1 wherein a is 5.

4. A silicone film forming polymer of claim 1 wherein a is 10.

5. A silicone film forming polymer of claim 1 wherein a is 20.

6. A silicone film forming polymer of claim 1 wherein b is 4.

7. A silicone film forming polymer of claim 1 wherein c is 1.

8. A silicone film forming polymer of claim 1 wherein c is 5.

9. A silicone film forming polymer of claim 1 wherein c is 10.

10. A process for applying color to the nail or skin which comprises addition of a film-forming silicone polymer which is made by the esterification reaction of;
(a) a difunctional organic polyol selected from the group consisting of

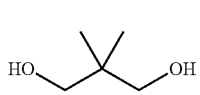 and 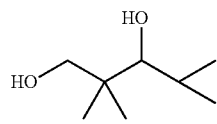

(b) a difunctional silicone polyol which conforms the following structure;

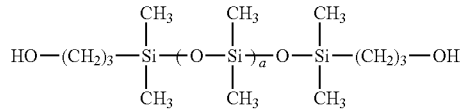

wherein;
a is an integer ranging from 1 to 20;
(c) a difunctional organic acid selected from the group consisting of;

HO—C(O)—(CH$_2$)$_b$—C(O)—OH and

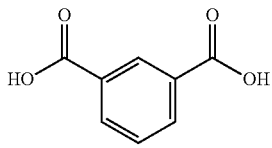

wherein;
b is an integer ranging from 1 to 10;
(d) a difunctional silicone acid which conforms the following structure;

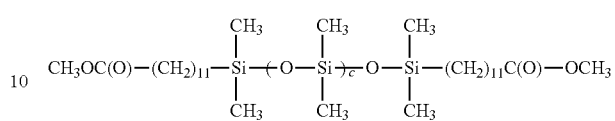

wherein;
c is an integer ranging from 1 to 20;
and
(e) trimellitic anhydride conforming the following structure;

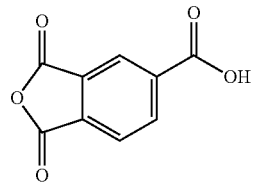 [SMILES: O=C(O)c1ccc2c(c1)C(=O)OC2=O]

additionally containing pigment and solvent.

11. The process of claim 10 wherein a is 1.

12. The process of claim 10 wherein a is 10.

13. The process of claim 10 wherein a is 20.

14. The process of claim 10 wherein b is 4.

15. The process of claim 10 wherein c is 1.

16. The process of claim 10 wherein c is 5.

17. The process of claim 10 wherein c is 10.

* * * * *